US00PP34859P2

(12) United States Plant Patent
Johnson, Jr.

(10) Patent No.: US PP34,859 P2
(45) Date of Patent: Dec. 20, 2022

(54) ***BEGONIA* PLANT NAMED 'DARK SIDE OF THE MOON'**

(50) Latin Name: ***Begonia* hybrid**
Varietal Denomination: Dark Side of the Moon

(71) Applicant: Ozzie W. Johnson, Jr., Marietta, GA (US)

(72) Inventor: Ozzie W. Johnson, Jr., Marietta, GA (US)

(73) Assignee: Plants Nouveau, Mobile, AL (US)

( * ) Notice: Subject to any disclaimer, the term of this patent is extended or adjusted under 35 U.S.C. 154(b) by 0 days.

(21) Appl. No.: 17/863,071

(22) Filed: Jul. 12, 2022

(51) Int. Cl.
*A01H 5/02* (2018.01)
*A01H 6/18* (2018.01)

(52) U.S. Cl.
USPC ..... Plt./343

(58) Field of Classification Search
USPC ..... Plt./263.1, 343
See application file for complete search history.

*Primary Examiner* — Karen M Redden
(74) *Attorney, Agent, or Firm* — Cassandra Bright

(57) ABSTRACT

A new and distinct cultivar of *Begonia* plant named 'Dark Side of the Moon' is disclosed, characterized by its distinctive large, green-black foliage with maroon undersides. Peduncles are long, holding most flowers above the foliage. Plants exhibit improved root hardiness and a rounded plant form. Immature flowers are cherry red, maturing to medium pink and white. The new cultivar is a *Begonia*, typically suited for garden and ornamental container use.

2 Drawing Sheets

Figure 1:
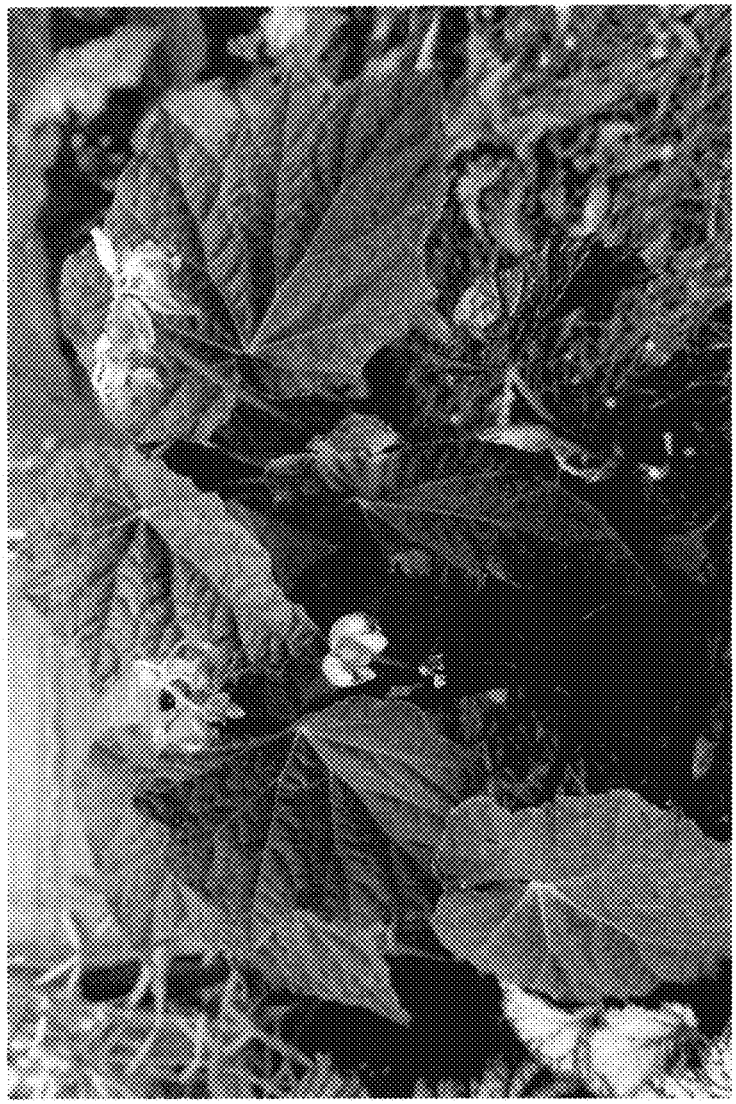

Latin name of the genus and species: *Begonia* hybrid.
Variety denomination: 'Dark Side of the Moon'.

BACKGROUND OF THE INVENTION

The new cultivar is a product of a planned breeding program. The new variety originated from an open-pollination of the seed parent, an unpatented, unnamed variety of *Begonia* hybrid with the pollen parent, a different *Begonia* hybrid, by the inventor during 2012. The crossing was made in Marietta, Ga. in the inventor's garden.

'Dark Side of the Moon' was selected by the inventor, in 2013 Marietta, Ga. in the inventor's garden.

After selection of the new cultivar, asexual reproduction of 'Dark Side of the Moon' was first performed at a hobbyist greenhouse in Alphretta, Ga. by leaf cuttings in 2014. 'Dark Side of the Moon' has since produced several generations and has shown that the unique features of this cultivar are stable and reproduced true to type.

SUMMARY OF THE INVENTION

The cultivar 'Dark Side of the Moon' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Dark Side of the Moon'. These characteristics in combination distinguish 'Dark Side of the Moon' as a new and distinct *Begonia* cultivar:

1. Distinctive green-black foliage with maroon undersides.
2. Root hardiness.
3. Large leaf size.

4. Cherry red immature flowers opening to medium pink and white.
5. Long peduncles holding flowers mainly above foliage.
6. Rounded plant form

PARENTAL COMPARISON

Plants of the new cultivar 'Dark Side of the Moon' are similar to the female parent in most horticultural characteristics. However, plants of 'Dark Side of the Moon' are larger and produce large foliage. Additionally, the new variety is more root hardy and has flowers with a different color pink.

The pollen parent cannot be specifically identified.

COMMERCIAL COMPARISON

Plants of the new cultivar 'Dark Side of the Moon' are similar to the commercial variety 'Metallic Mist' U.S. Plant Pat. No. 19,567 in most horticultural characteristics. However, 'Dark Side of the Moon' differs in the following:

1. The new variety has more colorful foliage than this comparator.
2. The new variety is more tolerant of heat and humidity than this comparator.
3. The new variety is more root hardy than this comparator.
4. The new variety has a larger leaf size than this comparator.
5. The new variety has a larger flower size
6. Plants of the new variety are larger than this comparator.

Plants of the new cultivar 'Dark Side of the Moon' are similar to the commercial variety 'Fireworks', unpatented, in most horticultural characteristics. However, 'Dark Side of the Moon' differs in the following:

1. The new variety is more root hardy than 'Fireworks'.
2. The new variety has a larger flower size than 'Fireworks'.
3. Plants of the new variety are larger and rounder than plants of 'Fireworks'.
4. The new variety has darker colored foliage than 'Fireworks'.

BRIEF DESCRIPTION OF THE PHOTOGRAPHS

The accompanying photograph in FIG. 1 illustrates in full color a typical plant of 'Dark Side of the Moon' grown outdoors in Loxley, Ala. This plant is approximately 1 year old, planted in the ground.

Figure 2:
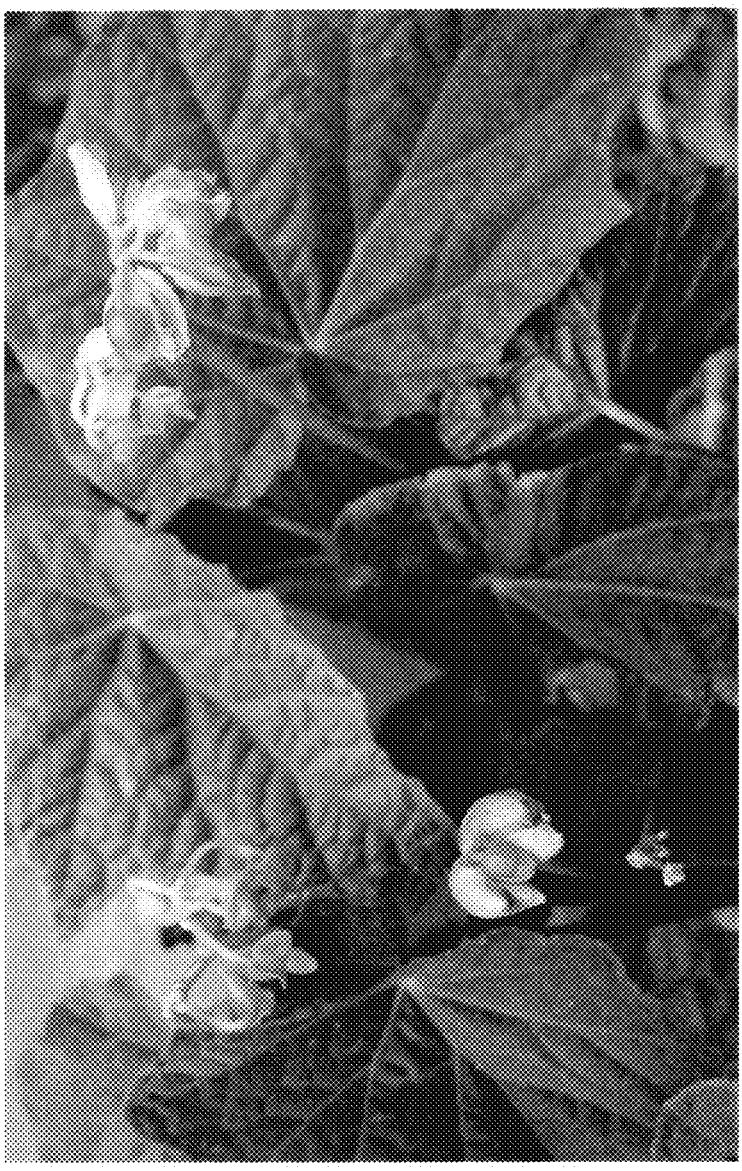

FIG. 2 illustrates a close-up view of the flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Dark Side of the Moon' plants grown in outdoors in Loxley, Ala. during Spring. Temperatures ranged from a low temperature about 55° F. at night to a high around 85° C. during the day. No artificial light, photoperiodic treatments or chemical treatments were given to the plants. Measurements and numerical values represent averages of typical plant types.

Botanical classification: *Begonia* hybrid 'Dark Side of the Moon'.

Age of the plant described: Approximately 1 year.

Container size of the plant described: 1-gallon commercial container.

PROPAGATION

Typically reproduced commercially by tissue culture. Leaf cutting propagation is also possible.

PLANT

Growth habit: Upright flowering tender perennial.

Pot size of plant described: 1-gallon.

Height: About 40 cm to 55 cm.

Plant spread: About 45 cm to 60 cm.

Growth rate: Moderate to rapid.

Branching characteristics: Basal branching, breaking into 2 lateral branches at about 12 to 18 cm with maturity.

Quantity of branches: About 15 to 20.

Characteristics of branches:

*Length*.—About 15 cm.

*Form*.—Round in cross section.

*Diameter*.—Approximately 1.0 cm.

*Color*.—Near RHS Yellow-Green 146D heavily flushed Greyed-Purple 183C.

*Texture*.—Mainly glabrous. Very sparse, irregular hirsute hairs, about 4 mm long colored near White 155C.

*Strength*.—Weak to moderate.

Internode length: About 5 to 7 cm.

FOLIAGE

Arrangement: Emerging basally, with maturity 2 emerging from a branch split.

*Quantity*.—Approximately 20 on a plant of this age.

*Average length*.—Average range 19 to 22 cm.

*Average width*.—Average range 18 to 20 cm.

*Shape of blade*.—Broad kidney shaped.

*Apex*.—Elongated acute.

*Base*.—Cordate.

*Margin*.—5 Shallow lobes with very shallow crenation.

*Texture of top surface*.—Glabrous, leathery.

*Texture of bottom surface*.—Glabrous. Very sparse hirsute hairs along main veins.

*Aspect*.—Puckered, overall flat.

*Color*.—Young foliage upper side: Near RHS Greyed-Green N189B. Young foliage under side: Near RHS Greyed-Purple 185B with a sheen 186C. Mature foliage upper side: Near RHS Greyed-Green N189A. Mature foliage under side: Near RHS Greyed-Purple 185B with a sheen 186C.

*Venation*.—Type: Palmate. Venation color upper side: Near RHS Greyed-Purple 185D. Venation color under side: Near RHS Greyed-Purple N186D.

*Petiole*.—Length: Average range 15 to 20 cm. Diameter: 7 to 8 mm. Color: Near RHS Yellow-Green 146D heavily flushed Greyed-Purple 183C. Greyed-Purple flush much stronger at base. Texture: Glabrous. Rarely a hirsute hair bout 4 mm long.

*Stipule description*.—1 or 2 per node, non-fleshy, becoming completely dry and papery before leaves fully expand. Length: Approximately 3.5 cm. Diameter: Approximately 1.8 cm. Color: Begins near Greyed-Red 185B, turning Greyed-Orange 166D when dry. Texture: Glabrous.

FLOWER

Flowering habit: Continuously flowering during Spring and Summer. Flowering begins in May, in the Gulf Coast of the US.

Inflorescence and flower type and habit: Single flowers arranged in axillary cymes. Cymes held slightly above or within foliage, approximately 2 to 4 flowers per cyme.

Cyme size:

*Diameter*.—Approximately 8 cm.

*Height*.—Approximately 4.5 cm.

Flowers per inflorescence: Average 8.

Flower longevity on plant: About 10 days, depending upon environmental conditions.

Persistent or self-cleaning: Self-Cleaning.

Bud:

*Shape*.—Ovate.

*Length*.—Approximately 2 cm, including bracts. Tepal bud alone about 1.2 cm.

*Diameter*.—Approximately 1 cm, including bracts. Tepal bud alone about 1.0 cm.

*Color*.—Tepal bud near RHS Red 51B. Immature bracts around bud colored near Red 53D.

Flower size:

*Diameter*.—Approximately 3.0 cm.

*Depth*.—Approximately 1.5 cm, including protruding stamens.

Tepals:
*Quantity*.—Approximately 5.
*Arrangement*. Rotate.
*Length*.—Approximately 1.7 cm.
*Width*.—Approximately 1.1 cm.
*Shape*.—Ovate.
*Apex*.—Obtuse.
*Base*.—Broad attenuate.
*Margin*.—Entire.
*Aspect*.—Slight upward curve.
*Texture, upper and lower surfaces*.—Glabrous.
*Appearance, upper and lower surfaces*.—Slightly iridescent.
*Color*.—When opening, upper surface: Near RHS Red 54B. When opening, lower surface: Near RHS Red 52B. Fully opened, upper surface: Near RHS Red 52C streaked White 155C. Fully opened, lower surface: Near RHS Red 52C streaked White 155C.

Flower bracts:
*Quantity per flower*.—2.
*Shape*.—Ovate, strongly concave.
*Length*.—Approximately 2.8 cm.
*Diameter*.—Approximately 1.7 cm, when manually flattened.
*Apex*.—Acute.
*Base*.—Truncate.
*Margin*.—Entire.
*Texture*.—Glabrous.
*Aspect*.—Strongly curved inward towards tepals.
*Color*.—Near RHS Green-White 2C when mature. Immature bracts near Red 51B.

Peduncles:
*Length*.—Average 16 cm.
*Diameter*.—Approximately 4 mm.
*Angle*.—About 15° to the lateral branch.
*Strength*.—Moderate, flexible.
*Texture*.—Glabrous.
*Color*.—Near RHS Yellow-Green N144A flushed Greyed-Red 180C towards base.

Pedicels:
*Length*.—Approximately 1.5 cm.
*Diameter*.—Approximately 3 mm.
*Angle*.—About 45° to the lateral branch.
*Strength*.—Moderate, flexible.
*Texture*.—Glabrous.
*Color*.—Near RHS Red 50D.

Fragrance: None.

REPRODUCTIVE ORGANS

Stamens:
*Number*.—8, arising from staminoidal column.

Anthers:
*Description*.—Fleshy, curly.
*Length*.—Free portion about 7 mm.
*Color*.—Near RHS Green-Yellow 1A.
*Pollen*.—Scant to none. Colored near Red 56D.

Pistil:
*Number*.—1.
*Length*.—Approximately 1.6 cm.
*Style*.—Length: Approximately 2 mm. Color: Near RHS Colored near Red 56D.
*Stigma*.—Shape: Linear. Color: Near RHS Colored near Red 56A. Ovary Color: Near RHS Yellow-Green 145B.

OTHER CHARACTERISTICS

Seeds: Not observed.

Disease/pest resistance: Moderate resistance and susceptibility to common diseases and pests of *Begonia* have been observed in the new variety.

Temperature tolerance: USDA Zone 7-9.

What is claimed is:

1. A new and distinct cultivar of *Begonia* plant named 'Dark Side of the Moon' as herein illustrated and described.

* * * * *